United States Patent [19]

Polito

[11] 4,081,245

[45] Mar. 28, 1978

[54] IMMUNOASSAY PROCEDURE EMPLOYING NOVEL IMMUNOCHEMICAL COMPOSITES

[75] Inventor: Alan J. Polito, Costa Mesa, Calif.

[73] Assignee: Beckman Instruments, Inc., Fullerton, Calif.

[21] Appl. No.: 682,808

[22] Filed: May 3, 1976

[51] Int. Cl.$^2$ .................... G01N 31/06; G01N 33/16
[52] U.S. Cl. .................... 23/230.6; 23/230 B; 195/63; 195/DIG. 11; 424/1; 424/1.5; 424/12; 260/112 B
[58] Field of Search ............... 23/230 B, 230.6; 424/1, 424/1.5, 12; 195/63, DIG. 11; 260/112 B

[56] References Cited

U.S. PATENT DOCUMENTS

| | | |
|---|---|---|
| 3,555,143 | 1/1971 | Axen .................... 424/1 |
| 3,645,852 | 2/1972 | Axen .................... 424/1 X |
| 3,867,366 | 2/1975 | Rubenstein .................... 424/1 X |
| 3,896,217 | 7/1975 | Johnson .................... 424/1 |
| 3,904,478 | 9/1975 | Dean .................... 195/DIG. 11 |
| 3,914,183 | 10/1975 | Johansson .................... 195/DIG. 11 |
| 3,947,352 | 3/1976 | Cuatrecasas .................... 195/DIG. 11 |
| 3,975,511 | 8/1976 | Vann .................... 424/1.5 |
| 3,980,765 | 9/1976 | Broussalian .................... 424/1 |
| 4,002,532 | 1/1977 | Weltman .................... 195/63 X |

OTHER PUBLICATIONS

Catt, et al., Biochem. J., 100:31c, (1966).
Wide, et al., Biochim. Biophys. Acta, 130:257, (1966).
Axen, et al., Nature (London), 214:1302, (1967).
Wide, Acta Endocrinol. (Copenhagen), Suppl. Mo. 142:207, (1969).
Ternynck, et al., F.E.B.S. Letters, 23:24, (1972).
Cuatrecasas, et al., Proc. Nat. ACA SEI U.S., 61:636, (1968).
Cambiaso, et al., Immunochemistry, 2:273, (1975).
Bolten, et al., Biochemica et Biophysica Acta, 329:318, (1973).
Ludwig, et al., Abst. 135th Meeting Am. Chem. Soc., 44c, (1959).
Wofsky, et al., Biochemistry, 2:104, (1963).
Dutton, et al., Biochem. and Biophys. Res. Comm., 23:703, (1966).
Wilcheck, et al., Molecular and Cellular Biochemistry, 4(3):181, (1974).
Immobilized Enzymes, Antigens, Antibodies and Peptides, edited by Howard H. Weetall, Marcel Decker, Inc., New York, New York, (1975), Chapters 4 and 9.

*Primary Examiner*—Sidney Marantz
*Attorney, Agent, or Firm*—Robert J. Steinmeyer; Robert S. Frieman

[57] ABSTRACT

A method of separating free from bound fractions in an immunoassay procedure of the type wherein a solution is contacted with a composite comprising a derivatized polysaccharide matrix covalently coupled to an antibody by a bifunctional coupling agent, wherein the improvement comprises selecting said bifunctional coupling agent from a group comprising

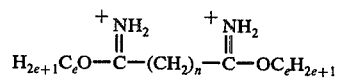

wherein $n$ is an integer from 1 to 6 and wherein $e$ is an integer from 1 to 2.

10 Claims, No Drawings

IMMUNOASSAY PROCEDURE EMPLOYING NOVEL IMMUNOCHEMICAL COMPOSITES

BACKGROUND OF THE INVENTION

1. Field of the Invention

This invention pertains to a method of separating free from bound fractions in an immunoassay procedure and to a novel immunochemical composite for use therein.

2. Description of the Prior Art

Solid phase radioimmunoassay (RIA) has become popular because the system in which both the antigen-antibody reaction and the separation of free and bound antigen can be achieved in a single step results not only in a simple and rapid RIA, but also eliminates a number of handling and other errors which are inherent in other separation techniques. K. J. Catt, H. D. Niall, and G. W. Tregear, Biochem. J., 100: 31c (1966), originally used as solid phase materials powdered polymers bearing reactive thiocyanate groups (—N=C=S) capable of forming covalent linkages with antibodies. Antibodies coupled to cyanogen-bromide-activated dextran and cellulose particles came into vogue as a result of the work of Wide, Porath, and Axen [L. Wide and J. Porath, *Biochem. Biophys. Acta*, 130: 257 (1966), R. Axen, J. Porath and S. Ernback, *Nature* (Lond.), 214: 1302 (1967), and L. Wide, *Acta Endocrinol.* (Copenhagen) Suppl. No. 142: 207 (1969)]. Alternatively, C. Ternynck and S. Azrameas, *F. E. B. S. Letts.*, 23: 24 (1972), used gluaraldehyde as a two-step bifunctional reactant to couple antibodies to the amide groups of polyacrylamide.

It has been well established that the efficiency of affinity adsorbents increase considerably when hydrocarbon spacers are introduced to separate the ligand from the solid matrix [P. Cuatrecasas, M. Wilcheck, and C. B. Anfinsen, Proc. Nat. Acad. Sci. U.S., 61: 636 (1968)]. The spacer is thought to increase the flexibility and mobility of the ligand allowing unhindered access of the protein to the ligand. Armed with this knowledge, C. L. Cambiaso, A. Gossinet, J. P. Vaerman, and J. F. Heremans, Immunochem., 12: 273 (1975), coupled gamma globulin fractions to glutaraldehyde-activated amino-hexyl derivatives of sepharose-4β, as shown in FIG. 1, and showed this procedure to produce useful immunosorbents.

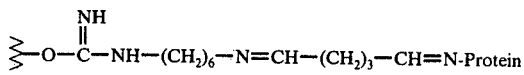

FIG. 1

It remains to be established whether purified antibodies or antibody containing gamma globulin fractions coupled to sepharose by this procedure will prove more efficient for antigen fixation than the same antibodies coupled to sepharose by means of the cyanogen bromide method. In this respect, A. E. Bolten and W. H. Hunter, *Biochemica et Biophysica Acta*, 329: 318 (1973), reported that recovery of antibody activity tends to be higher on cyanogen bromide activated solid preparations of antisera to haptens and small peptides than to similar solid phase preparations of antisera to large molecular weight protein hormones (see FIG. 2).

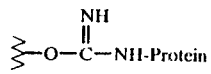

FIG. 2

Although it may seem reasonable that solid phase preparations of antisera to large molecules produced by procedures similar to Cambiaso et al., supra, might yield a better recovery of antibody activity than those solid preparations produced without a spacer arm, there exists two disadvantages in the chemical procedures used at this time to covalently link antibodies to solid matrices. First, in many cases, the exact nature of the chemical reactions are not well established and, secondly, the antibodies immobilized may be bound to the solid matrix in a random manner and thus the possibility of the coupling involving an "essential" amino acid residue is increased.

As far back as 1959, M. L. Ludwig and Hunter, *Abst 135th Meeting Am. Chem. Soc.*, 44c (1959), reported on the reaction of substituted imido esters with typical α and ε-amino groups of glycylglycine and ε-aminocaproic acid to form amidines (see FIG. 3).

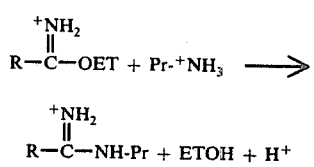

FIG. 3

These authors stated that the reaction proceeds rapidly in an aqueous solution near neutral pH even at 1° C., and under these conditions the imidoester reagent does not react with model compounds containing sulfhydryl groups, phenolic groups, imidazole groups, or peptide bonds. Further, they noted that the net charge of the peptide is unchanged through most of the pH range, the amidine function having a pk near 12.

in 1963 L. Wofsky and S. J. Singer, Biochem., 2:104 (1963), exhaustively amidinated various proteins and found the reaction to be very specific for lysine residues. Furthermore, they reported that extensive amidination produces remarkably few detectable effects on the biological activity of antibodies. The concluded that lysine is not critically involved in the reactive sites of any of the antibodies examined (anti-bovine serum albumin (anti-BSA), anti-benzene-arsonate, anti-D-benzoylaminophenyl acetate, anti-SIII, anti-DNP, and anti-β-lactoside).

Later in 1966, A. Dutton, M. Adams, and S. J. Singer, *Biochem. and Biophys. Res. Comm.*, 23:730 (1966), extensively modified anti-DNP antibodies with the crosslinking agent diethylmalonimidate dihydrochloride and similarly reported quantitative retention of antibody activity (see FIG. 4).

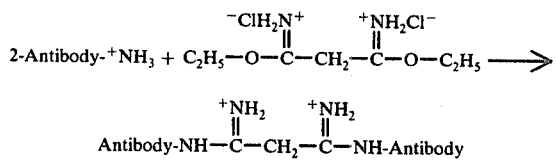

$$+ 2C_2H_5OH + 2HCl$$

FIG. 4

Although the work of Ludwig et al., Wofsky et al., and Dutton et al. has been around for what would in scientific circles be recognized as a considerable number of years, no one has transplanted their work into the art of immunoassay procedures. One reason for this may be that skilled artisans prefer not to use charged derivatized matrices. For example, M. Wilchek and T. Myron, *Molecular and Cellular Biochemistry*, Vol. 4, No. 3, p. 181 (1974), report that positively charged derivatized matrices cause nonspecific adsorption and therefore are not desirable to be used in immunoassay procedures. Therefore, those skilled in the art of immunoassay procedures may have considered the employment of the above imidoester reagents undesirable in that said reagents would produce positively charged solid phase immunochemical composites.

It has been discovered that immunochemical composites containing positively charged imidoesters as coupling agents are excellent means for separating free from bound fractions in an immunoassay procedure.

SUMMARY OF THE INVENTION

This invention encompasses a method of separating free from bound fractions in an immunoassay procedure of the type wherein a solution is contacted with a composite comprising a derivatized polysaccharide matrix covalently coupled to an antibody by a bifunctional coupling agent, wherein the improvement comprises selecting said bifunctional coupling agent from a group comprising $$H_{2e+1}C_eO-\overset{+NH_2}{\overset{\|}{C}}-(CH_2)_n-\overset{+NH_2}{\overset{\|}{C}}-OC_eH_{2e+1}$$

wherein n is an integer from 1 to 6 and wherein e is an integer from 1 to 2.

Also encompassed in this invention is an immunochemical composite for separating free from bound fractions in an immunoassay procedure of the type having a derivatized polysaccharide matrix covalently coupled to an antibody by a bifunctional coupling agent, wheren the improvement comprises selecting said bifunctional coupling agent from a group comprising $$H_{2e+1}C_eO-\overset{+NH_2}{\overset{\|}{C}}-(CH_2)_n-\overset{+NH_2}{\overset{\|}{C}}-OC_eH_{2e+1}$$

wherein n is an integer from 1 to 6 and wherein e is an integer from 1 to 2.

DESCRIPTION OF THE PREFERRED EMBODIMENTS

The immunoassay procedure of this invention entails contacting a solution containing free and bound fractions with a novel immunochemical composite via techniques well known to those skilled in the art of immunoassay and thereby separating the free from the bound fractions. See D. M Weir, "Immunology for Undergraduates", Churchill Livingstone, Edinburgh, England (1973) and J. G. Ratcliffe, *British Medical Bulletin*, 30:32 (1974), said publications being incorporated herein in toto by reference. Preferably, the immunoassay procedure is an RIA procedure which techniques are also well known to those skilled in the art. See C. S. Skelley L. P. Brown, and P. K. Besch, "Radioimmunoassay", *Clinical Chemistry*, Vol. 19, No. 2, 146 to 186 (1973), said publication being incorporated herein in toto by reference.

The novel immunochemical composite within the scope of this invention comprises a derivatized polysaccharide matrix covalently coupled to an antibody by a bifunctional coupling agent. The polysaccharide matrix can be any matrix having a plurality of hydroxyl groups attached thereto, as well as derivatives thereof. Preferred polysaccharide matrices include celluosic polymers, dextran polymers, agarose, and derivatives thereof. Cellulosic polymers and derivatives thereof are the polysaccharide matrices of choice.

The polysaccharide matrices can be activated by any suitable method known to those skilled in the art. Exemplary reagents suitable for activating the polysaccharide matrix include cyanogen halide, epihalohydrin, haloacetyl halides, and divinylsulphone. See F. A. Patty, *Industrial Hygiene and Toxicology*, Vol. 2, p. 634, Interscience, New York, N. Y. (1949), R. Axen, J. Porath, and S. Ernback, Nature (Lond.), 214: 1302 (1967), W. Rosner and R. N. Smith, Biochem., 14: 4813 (1975), A. Jagendorph, A. Patchornik, and M. Sela, *Biochimica et Biophysica Acta*, 78: 516 (1963), and J. Porath and L. Sundberg, *Nature New Biol.*, 238: 216 (1972), said publications being incorporated herein in toto by reference. Preferably, a cyanogen halide or an epihalohydrin reagent is used to activate the polysaccharide matrix. More preferably, the polysaccharide matrix is activated by an epihalohydrin reagent or mixture thereof and most preferably, the polysaccharide matrix is activated by epichlorohydrin.

An α, ω-diaminospacer is then coupled to the above activated polysaccharide matrix via one of the α,ω-diaminospacer's amino groups thereby forming a derivatized polysaccharide matrix. To illustrate this point, if the polysaccharide matrix has been activated by a cyanogen halide reagent, the derivatized polysaccharide matrix will have the formula $$\text{matrix-O}-\overset{NH}{\overset{\|}{C}}-NH-Y-NH_2$$

wherein matrix is a polysaccharide matrix as defined above and wherein Y is a spacer. Exemplary spacers include $-(CH_2)_m-$, $-(CH_2)_b-NH-(CH_2)_c-$,

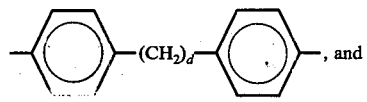, and

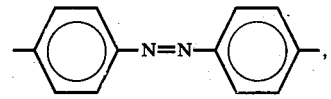, wherein m is an integer from 1 to 12, preferably from 4 to 6, wherein b and c independently are integers from 1 to 6, preferably 2 to 3, and wherein d is an integer from 1 to 10, preferably 2 to 4. Preferably, Y is $-(CH_2)_m-$.

As a further illustration of a derivatized polysaccharide matrix, if the polysaccharide matrix has been activated by an ephihalohydrin reagent, the derivatized polysaccharide matrix will have the formula

wherein matrix and Y are as defined above.

The antibody to which the derivatized polysaccharide matrix is covalently coupled can be either a primary antibody or a secondary antibody. Since this invention's sole requirement is that the antibody possess a lysine residue, virtually all primary and secondary antibodies can be covalently coupled to the derivatized polysaccharide matrix because all antibodies possess such lysine residues. Preferably, the antibody is a secondary antibody.

The crux of this invention is the use of imidoesters as the coupling agent for the novel immunochemical composite. The imidoester has the general formula

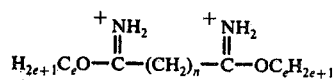

wherein $n$ is an integer from 1 to 6, preferably from 4 to 6, and wherein $e$ is an integer from 1 to 2. The use of these imidoesters enables one to covalently attach antibodies to solid supports through known chemical reactions which immobilize both primary and secondary antibodies through their lysine residues which in most instances are not essential for immunological activity. Further, the presence of a positively charged matrix does not cause adverse nonspecific adsorption onto this invention's novel immunochemical composite.

The novel immunochemical composites within the scope of this invention can be prepared in accordance with the following general procedure. An activating reagent is contacted with a polysaccharide matrix in a solution having a desirable pH. The pH can be in a general range from about 7.5 to about 10.0 with the particular pH being dictated by the activating reagent and polysaccharide matrix being used. The reaction can be allowed to proceed at room temperature. The activating reagent is allowed to remain in contact with the polysaccharide matrix for a sufficient period of time, from about 5 minutes to 5 hours, to enable the matrix to become activated. The excess activating reagent is removed from the activated polysaccharide matrix by washing said matrix with a suitable medium, e.g., water, buffer (e.g., sodium bicarbonate), etc. The activated matrix is then suspended in a suitable medium, e.g., an aqueous solution of dimethylformamide. The desired $\alpha,\omega$-diaminospacer is then added to the suspended activated polysaccharide matrix and the reaction is allowed to proceed for about 1 to 10 hours at room temperature. The excess $\alpha,\omega$-diaminospacer is removed from the derivatized polysaccharide matrix by washing said matrix with a suitable medium, e.g., a solution of dimethylformamide, followed by a washing with a suitable buffer, e.g., a sodium bicarbonate buffer. After this double washing procedure, the derivatized polysaccharide matrix is suspended in a suitable buffer, e.g., a sodium bicarbonate buffer.

The bifunctional coupling agent or mixture thereof is dissolved in a basic solution at about 4° C. If necessary, the pH is adjusted to about 8 to 9. The suspended derivatized polysaccharide matrix is then contacted with the dissolved bifunctional coupling agent and the mixture is rotated at about 4° C. for 1 to 5 hours.

After removing the excess bifunctional coupling agent, the coupled derivatized polysaccharide matrix is suspended in a mixture containing a suitable buffer, e.g., a sodium bicarbonate buffer, and a primary or secondary antibody function. The mixture is rotated for about 10 to about 24 hours in a cold environment. The immunochemical composite is then thoroughly washed with a suitable buffer, e.g., a sodium bicarbonate buffer, and then suspended in a suitable buffer having a pH of about 8, e.g., a barbital buffer containing about 0.1% gelatin.

The novel immunochemical composite within the scope of this invention and as prepared by the above general procedure has the schematic structure

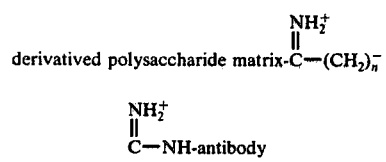

wherein derivatized polysaccharide matrix, $n$, and antibody are as defined above. The preferred immunochemical composite within the scope of this invention has a formula

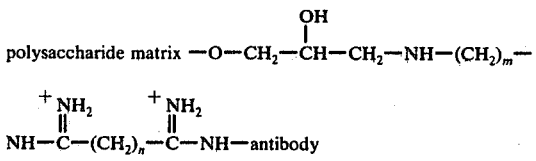

wherein polysaccharide matrix, $m$, $n$, and antibody are as defined above.

The following examples are provided for the purpose of further illustration only and are not intended to be limitations on the disclosed invention.

EXAMPLE 1

Epichlorohydrin (3 ml) was added to a mixture of 6 gms of microcrystalline cellulose Type 50 (50 $\mu$ average particle size) in 30 ml of 1N sodium hydroxide with vigorous stirring at room temperature. After 2 hours, the excess epichlorohydrin was removed by washing with 1 liter of water. The washed activated cellulosic matrix was then suspended in 60 ml of a 50% aqueous solution of dimethylformamide. To this suspended activated matrix was added 0.85 gms of 1.6-hexanediamine. The reaction was allowed to proceed with stirring for 2 hours at room temperature and then the excess 1,6-hexanediamine was removed by washing with 1 liter of a 50% aqueous solution of dimethylformamide. After washing with 1 liter of 0.1M sodium bicarbonate, the derivatized cellulosic matrix was suspended in 0.1M sodium bicarbonate to give a 1:1 mixture of derivatized matrix to sodium bicarbonate.

Dimethyladipidate (DMA; 0.735 gm; 3 m moles) was dissolved in 0.6 ml of cold 5N sodium hydroxide solution with stirring at 4° C. After the addition of cold 0.1 M sodium bicarbonate the pH was adjusted to 8.5 with 1N sodium hydroxide. To this solution was added 6 ml of 0.1M sodium bicarbonate containing 0.8 to 1.0 grams of derivatized cellulose and the mixture was rotated at 4° C. for 2 hours.

After the removal of excess dimethyl adipimdate, the coupled derivatized cellulosic matrix was suspended in 9 ml of 0.1M sodium bicarbonate (4° C.) and 1.1 ml of goat antirabbit gamma globulin fraction (42.82 mg/ml) in 0.1M sodium bicarbonate (4° C.) and the mixture was rotated in a cold room. The immobilized second antibody was then thoroughly washed with 0.1M sodium carbonate and finally suspended in 10 ml of barbital buffer, pH 8.0, containing 0.1% gelatin.

Another immunochemical composite was also prepared according to the procedure of Example 1 except that the bifunctional coupling agent used was dimethyl suberimidate dihydrochloride (DMS) instead of the DMA of Example 1.

EXAMPLE 2

Microcrystalline cellulose type 50 (1 gm) was added to a solution of 1.0 gm of cyanogen bromide in water at room temperature. The pH of the mixture was immediately adjusted to about 11.0 with 2N sodium hydroxide and maintained at this pH for 6 to 12 minutes by the controlled addition of 2N sodium hydroxide. After the pH stabilized at about 11, the mixture was allowed to stand an additional 5 to 10 minutes before the activated cellulosic matrix was washed with 1.1 liters of 0.1N sodium bicarbonate at 4° C. to remove the excess cyanogen bromide.

The thoroughly washed activated cellulosic matrix was then suspended in 10 ml of 0.1N sodium bicarbonate and about 47 mgms of goat antirabbit gamma globulin in 1.3 ml of 0.1N sodium bicarbonate was added thereto. The suspension was then mixed at room temperature overnight.

The following day the immunochemical composite was washed with 600 ml of 0.1N sodium bicarbonate and 100 ml of barbital buffer (pH 8.0) containing 0.1% gelatin. Finally, the composite was suspended in about 10 ml of the above gelatin containing barbital buffer.

EXAMPLE 3

Solid phase preparations of activated microcrystalline cellulose as prepared in examples 1 and 2 were titered against $^{125}$I-labeled rabbit gamma globulin as follows:

200λ — barbital buffer pH 8.0 containing 3.5% BSA
100λ — $^{125}$I-labeled rabbit gamma globulin containing 0.1% normal rabbit serum
100λ — barbital buffer pH 8.0
200λ — solid phase second antibody preparation Each tube was incubated at room temperature for ½ hour with shaking and subsequently centrifuged for 20 minutes at 1,000 × g.

The units of activity were calculated from the largest dilution, i.e., titer, of solid phase second antibody that resulted in maximal binding of the labeled antigen. The formula used to calculate the units of activity is as follows:

$$\frac{\frac{1}{\text{titer}}}{\text{sample size}} \times \frac{\text{total volume of solid phase antibody preparation}}{} = \text{Units of Activity}$$

wherein the sample size in our example is 200λ (0.2 ml) and wherein the total volume of solid phase secondary antibody preparation is 10 ml. Since these titers were done in the presence of 100λ of 0.1% normal rabbit serum, one actually looks for the largest dilution of solid phase second antibody capable of binding about 1 microgram of rabbit gamma globulin. The results of these calculations are listed in Table I. As Table I clearly depicts, the titer of the goat anti-rabbit antisera coupled to the DMA derivatized cellulose was far superior to the corresponding cyanogen bromide (CNBr) coupled preparation of microcrystalline cellulose.

EXAMPLE 4

Derivatized cellulose as prepared in Example 2 and the DMS version of Example 1 were titered against $^{125}$I-thyroxine in the presence of about 1 microgram of rabbit gamma globulin as follows:

20λ — barbital buffer pH 8.0 containing 3.5% BSA
100λ — $^{125}$I-thyroxine in barbital buffer pH 8.0 containing 2% BSA
100λ — rabbit antisera against thyroxine at a dilution of 1 per 1,000 in barbital buffer pH 8.0.
200λ — solid phase second antibody preparation.

Each tube was incubated at room temperature for about ½ hour with shaking and subsequently centrifuged for 20 minutes at 1000 × g. The precipitates where then suspended in 1.0 ml of barbital buffer pH 8.0 containing 2% BSA and centrifuged for 20 minutes at 1000 × g. In these experiments the labeled thyroxine is immunologically bound to its specific antibodies which are present as a fraction of about 1 microgram of rabbit gamma globulin. Thus, in this example, one is able to indirectly measure the units of second antibodies bound to the cellulose matrix by calculating the largest dilution of solid phase second antibody preparation to give the maximal binding of labeled-thyroxine.

Table I also depicts the results of this data. As Table I clearly shows, the DMS experiments compare favorably to the origin of DMA data and both preparations far surpass their corresponding cyanogen-bromide controls. Similar improvements in the amount of units of activity recovered also result when the novel immunochemical composites within the scope of this invention contain primary antibodies instead of secondary antibodies.

Therefore, this invention's positively charged novel immunochemical composites containing bifunctional imidoesters as coupling agents must be considered a marked improvement over prior art immunochemical composites used in immunoassay procedures.

Table I

| Support | Protein Concentration of Antibody Containing Gamma Globulin Fraction | Titer | Units of Activity Recovered | Percent Increase in Activity Recovered |
|---|---|---|---|---|
| *A. 1 gram cyanogen bromide activated microcrystalline cellulose | 47 mg of goat anti-rabbit gamma globulin | 1/2.3 | 115 | — |
| A. 1 gram dimethyl adipidimate activated microcrystalline cellulose | 47 mg of goat anti-rabbit gamma globulin | 1/16.5 | 850 | 739 |
| **B. 1 gram cyanogen bromide activated microcrystalline | 40 mg of goat anti-rabbit gamma globulin | 1/3.2 | 160 | — |

Table I-continued

| Support | Protein Concentration of Antibody Containing Gamma Globulin Fraction | Titer | Units of Activity Recovered | Percent Increase in Activity Recovered |
|---|---|---|---|---|
| cellulose | | | | |
| B. 1 gram dimethyl suberimidate activated microcrystalline cellulose | 40 mg of goat anti-rabbit gamma globulin | 1/16 | 800 | 500 |

*A - label $^{125}$I-rabbit gamma globulin
**B - label $^{125}$I-thyroxine

Based on this disclosure, many other modifications and ramifications will naturally suggest themselves to those skilled in the art of immunoassay procedures. These are intended to be comprehended as within the scope of this invention.

The embodiments of the invention in which an exclusive property or privilege is claimed are defined as follows:

1. A method of separating free from bound fractions in an immunoassay procedure of the type wherein a solution is contacted with a immunochemical composite comprising a derivatized polysaccharide matrix covalently coupled to an antibody by a bifunctional coupling agent, wherein the improvement comprises selecting said bifunctional coupling agent from a group consisting of

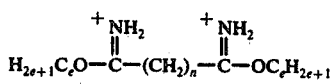

wherein $n$ is an integer from 1 to 6 and wherein $e$ is an integer from 1 to 2.

2. The method of claim 1 wherein said immunochemical composite has a formula

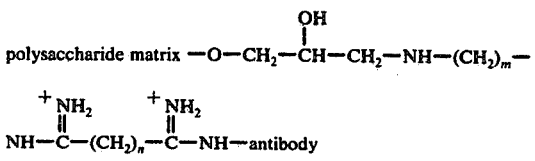

wherein $m$ is an integer from 1 to 12.

3. The method of claim 2 wherein said polysaccharide matrix is selected from the group consisting of cellulosic polymers, dextran polymers, agarose, and derivatives thereof, wherein $m$ is an integer from 4 to 6, and wherein $n$ is an integer from 4 to 6.

4. The method of claim 3 wherein said antibody is a secondary antibody.

5. The method of claim 4 wherein said immunoassay procedure is a radioimmunoassay procedure.

6. The method of claim 1 wherein said immunoassay procedure is a radioimmunoassay procedure.

7. An immunochemical composite for separating free from bound fractions in an immunoassay procedure of the type having a derivatized polysaccharide matrix covalently coupled to an antibody by a bifunctional coupling agent, wherein the improvement comprises selecting said bifunctional coupling agent from a group consisting of

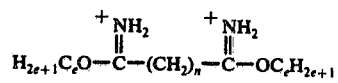

wherein $n$ is an integer from 1 to 6 and wherein $e$ is an integer from 1 to 2.

8. The immunochemical composite of claim 7 having a formula

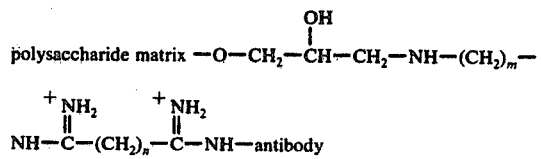

wherein $m$ is an integer from 1 to 12.

9. The immunochemical composite of claim 8 wherein said polysaccharide matrix is selected from the group consisting of cellulosic polymers, dextran polymers, agarose, and derivatives thereof, wherein $m$ is an integer from 4 to 6 and wherein $n$ is an integer from 4 to 6.

10. The immunochemical composite of claim 9 wherein said antibody is a secondary antibody.

UNITED STATES PATENT AND TRADEMARK OFFICE
CERTIFICATE OF CORRECTION

PATENT NO. : 4,081,245

DATED : March 28, 1978

INVENTOR(S) : Alan J. Polito

It is certified that error appears in the above–identified patent and that said Letters Patent are hereby corrected as shown below:

Column 10, Claim 8, Line 40, delete "ps"

Signed and Sealed this

Eighth Day of August 1978

[SEAL]

Attest:

RUTH C. MASON
*Attesting Officer*

DONALD W. BANNER
*Commissioner of Patents and Trademarks*